United States Patent [19]
Mollstam et al.

[11] Patent Number: 6,098,795
[45] Date of Patent: Aug. 8, 2000

[54] DEVICE FOR ADDING A COMPONENT TO A PACKAGE

[76] Inventors: Bo Mollstam; Ivan A. Casas, both of 6213 Angus Dr., Suite D, Raleigh, N.C. 27613

[21] Appl. No.: 09/265,453

[22] Filed: Mar. 10, 1999

Related U.S. Application Data

[63] Continuation-in-part of application No. 08/949,465, Oct. 14, 1997, abandoned.

[51] Int. Cl.[7] .................................................. B65D 25/08
[52] U.S. Cl. .......................................... 206/222; 206/219
[58] Field of Search .................................. 206/219, 222; 222/80, 145.1, 145.5; 215/DIG. 8

[56] References Cited

U.S. PATENT DOCUMENTS

| | | | |
|---|---|---|---|
| 2,631,521 | 3/1953 | Atkins, Jr. .......................... | 215/DIG. 8 |
| 3,326,363 | 6/1967 | Bennett et al. . | |
| 3,349,965 | 10/1967 | Krugger ..................................... | 222/80 |
| 3,415,360 | 12/1968 | Baumann et al. ....................... | 206/222 |
| 3,779,372 | 12/1973 | de Lloret . | |
| 3,968,820 | 7/1976 | Kolb et al. ........................... | 215/DIG. 8 |
| 4,074,827 | 2/1978 | Labe, III . | |
| 4,609,369 | 9/1986 | Ball ......................................... | 206/219 |
| 4,785,931 | 11/1988 | Weir et al. . | |
| 4,874,618 | 10/1989 | Seaborne et al. . | |
| 5,035,320 | 7/1991 | Plone . | |
| 5,255,812 | 10/1993 | Hsu .......................................... | 206/222 |
| 5,290,574 | 3/1994 | Jamieson et al. . | |
| 5,370,222 | 12/1994 | Steigerwald et al. . | |
| 5,419,429 | 5/1995 | Zimmerman et al. . | |
| 5,884,759 | 3/1999 | Gueret ..................................... | 206/222 |

FOREIGN PATENT DOCUMENTS

| | | | |
|---|---|---|---|
| 3-98871 | 4/1991 | Japan ..................................... | 206/222 |

*Primary Examiner*—David T. Fidei
*Attorney, Agent, or Firm*—Lynn E. Barber

[57] ABSTRACT

A device that may be used for adding a selected first component to a second component that is in a main package, which device keeps the first component from the second component until a selected time before use. The device includes a delivery package which is mountable on the outside surface of the main package, and has a delivery opening, a control opening, and a cavity extending between the delivery opening and the control opening. When there is a first component, a compartment that contains this component is mounted inside the cavity so that it seals the delivery opening with a puncturable seal. A puncturer controllable by a user through the control opening is used for cutting through the compartment, including the puncturable seal, and the package to which the delivery package is mounted to release the first component into the main package at the selected time.

14 Claims, 5 Drawing Sheets

DEVICE FOR ADDING A COMPONENT TO A PACKAGE

CROSS-REFERENCE TO RELATED APPLICATIONS

This is a continuation-in-part of application Ser. No. 08/949,465, filed Oct. 14, 1997, now abandoned the disclosure of which is incorporated herein by reference.

BACKGROUND OF THE INVENTION

1. Field of the Invention

This invention relates to packages, and in particular, pertains to packages having two compartments and that may be used to keep two components separate until use.

2. Description of the Related Art

Many different types of packages have been designed to enable product components to be kept separate until use and, in some cases, to allow one component to remain sterile until use of the product. In one type of two-compartment package, a stopper or other means is placed in the hole between the two compartments. For example, the two-compartment container of Haim (U.S. Pat. No. 5,417,321) comprises a one-piece container having two compartments assembled one upon another interlinked by a stoppered opening.

Other two-compartment packages utilize a perforating unit to allow the two previously separated components to mix. See, for example, the patents of Goncalves (U.S. Pat. No. 5,170,888 which has a glass defining a first compartment, which is provided with a neck upon which is mounted a bottle defining a second compartment, with a membrane between the two compartments that is perforated when a perforating unit is displaced relative to the glass, and U.S. Pat. No. 4,757,916 which has two units separated by a cover perforatable as a result of the manipulation of a mixing perforator). The two-part container of Wiegner (U.S. Pat. No. 4,103,772) has a frangible partition of coated aluminum foil dividing the compartments and a piercing member mounted on a resilient portion transversely directed toward the partition. In the patent of White (U.S. Pat. No. 4,637,934) rigid penetrating means are used to penetrate a compartment closing diaphragm to allow nursing liquid to flow from the compartment to a communicating, attached nipple.

Two compartment packages have also been previously developed which have an opening device attached to the top of the package and are provided with a screw cap and a cylinder jacket shaped supporting ring. The cylinder jacket shaped supporting ring is attached to the top of the package by means of a fixing flange externally surrounding the opening disc and is provided on its inner surface with a raised thread. The ring surrounds the external thread of the plastic screw cap. A cutter is integrally molded onto the free edge of the screw cap, and is provided with a front cutting edge which passes at an angle through the free edge.

For such products as two-part epoxy glues, two compartments are also needed to keep the products from reacting, as in the patent of Wilkinson et al. (U.S. Pat. No. 4,786,279).

The dispenser of Renault (U.S. Pat. No. 5,564,600) has two compartments separated by a sealing member sealed against a seat, so that movement of one of the containers relative to the other causes the sealing member to move away from the seat and form an annular passage between the sealing member and the seat.

The co-pending application (Ser. No. 08/949,465) provides a two-compartment package which keeps a first component separate from a liquid component until use, so that the first component does not become wetted until just before use. The two-compartment package keeps at least one of the components sterile until just before use, at or before which time, the two components may be easily mixed. The prior invention can thus be used for containers for the separate packaging of dried microbial cultures which are to be added to a food, liquid nutrition, medicine, or beverage product just before consumption, for the separate packaging of carbonation tablets from a liquid until just before consumption, and for separate packaging of vitamins or other unstable components before addition to a beverage, liquid nutrition, medicine or beverage before consumption.

In some cases, such as with enteral nutrition bags, there is a need to provide a means for adding a selected separate first component to a package after manufacture of the package and/or at a location on the package, which component may vary in concentration and/or composition, depending, for example, on the patient's history and diagnosis. Providing a means of attaching a first compartment to a package after both the first compartment and package have been manufactured allows a user to select both a particular first component to add to a package and the time and place of addition of the first component to the package. There is also need to have the capability to add beverage additives (for example, vitamins) to liquid beverage bottles at or just before the time the beverage is consumed.

It is therefore an object of the invention to provide a device and means for adding a selected component to a package, thus forming a two-compartment container that keeps a first component, which may be moisture sensitive, from a second component, preferably a liquid, until a selected time before use.

It is also an object of the invention to provide a device and means for adding a means of access to a beverage package.

Other objects and advantages will be more fully apparent from the following disclosure and appended claims.

SUMMARY OF THE INVENTION

The invention herein is a device and means for adding a selected component to a main package, thus forming a two-compartment container that keeps a first component, which may, for example, be moisture sensitive, from a second component, preferably a liquid, until a selected time before use. The use of the invention also includes addition of other first components, which for any other reasons, should not or cannot be added until a selected time before use. The invention also includes the separate addition of one or more first components to a previously empty main package.

The first embodiment of the device preferably comprises a delivery package that is mountable on the outside surface of a main package, preferably containing a second component in a compartment inside a cavity in the delivery package. A puncture means is provided for cutting through the compartment and the main package to gain access to the main package, for example, to release the first component from the compartment into the main package. The main package may be a bag, such as an enteral bag in the preferred use of the first embodiment. In the second embodiment of the invention, the main package preferably is for holding a liquid beverage, and the delivery package is attached to the main package during the manufacturing process.

Other objects and features of the inventions will be more fully apparent from the following disclosure and appended claims.

DETAILED DESCRIPTION OF THE INVENTION AND PREFERRED EMBODIMENTS THEREOF

The present invention provides a device 10 comprising a main package 12 and a delivery package 14 (FIGS. 1–2, 8–9, 16–17). It is understood that by use of the terms "main" package and "delivery" package as used herein, no limitation is placed on the absolute or relative sizes of the packages. The terms are used merely to distinguish the two packages by difference in function and structural characteristics, with the main package including packages known in the prior art for holding substances and the delivery package preferably designed for holding a first component to be added to the main package and for containing the puncturer 16.

The device 10 of the invention may be used for adding a selected first component C1 to a main package 12. The device 10 of the invention forms a two-compartment container that may be used to keep the first component, which may be sensitive as discussed below, from the main package 12, and preferably from a second component C2, preferably a liquid, that is in the main package 12, until a selected time before use. The method of the invention also includes the separate addition of one or more first components to a previously empty main package 12.

The device 10 comprises the delivery package 14 and a puncturer 16 to cut through delivery package 14 and main package 12. The puncturer 16 cuts through a compartment 18 that is located in delivery package 14, when there is a first component C1 in compartment 18, to release the first component C1 into main package 12.

Figure 1:
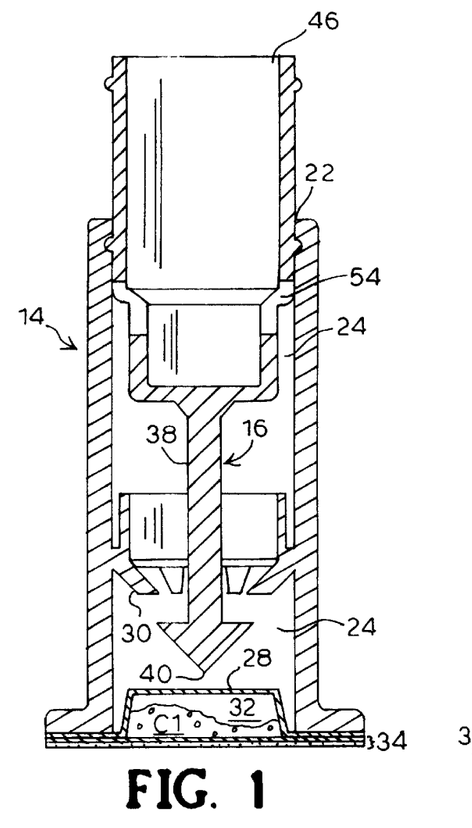
FIG. 1 is a partial cross-sectional view of the first embodiment of the invention, which is attachable to a container, before the puncturer is lowered.
Figure 2:
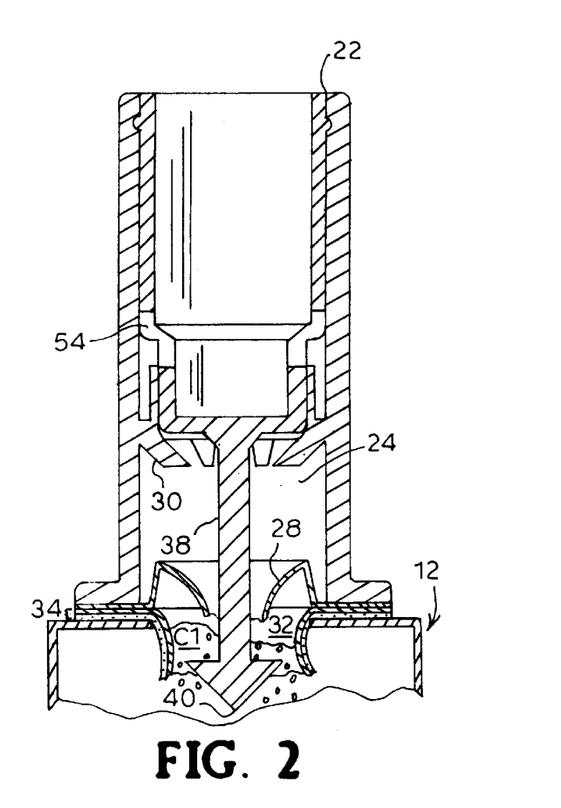
FIG. 2 is a partial cross-sectional view of the first embodiment of the invention, which is attached to a container, after the puncturer is lowered.

In the first embodiment, shown in FIGS. 1–2, the delivery package 14 together with puncturer 16 is mountable on the outside surface of main package 12 at any time prior to use. In the second embodiment of the invention herein shown in FIGS. 8–9, the separately manufactured delivery package 14 and puncturer 16 are together structured to attach to a bottle-top, and are generally affixed to main package 12 by a manufacturer. In the third embodiment shown in FIGS. 16–17, the delivery package 14 is externally mounted on a main package 12, and is structured so that an external puncturer can be mounted on the delivery package 14 and utilized, as discussed below.

The invention is primarily designed for addition of a selected, sensitive first component C1, preferably located in compartment 18, to a liquid located in main package 12. The term "selected" first component Cl as used herein includes first component(s) chosen for a particular use, e.g., addition to the enteral nutrition bag of a person requiring additional vitamins or antibiotics, or having a particular volume or concentration, and the like. The first component may be a single compound, mixture, solution, capsule, powder, or any other containable component(s) to be added to a main package that preferably contains a second component (which may in turn be any containable compound(s) to which the first component may be added to result in a useful product. The ability to select from an assortment of prepackaged first components in the first embodiment herein allows the purchaser to purchase and store first and second components separately, for example, to keep non-perishable second components at room-temperature, and to keep first compartments, each of which has one of any number of assorted first components under appropriate, possibly separate, storage, for later addition to the second component. When the first component C1 comprises microorganism cells, the first component is preferably in a new powdered formulation as described below.

The term "sensitive" includes first components which are moisture-sensitive, or which interact with the second component, for example, by forming by-products that change the usefulness of the combined components, for example, from initially useful to too weak, due, for example, to loss or change of strength or value with time after the combination of components. "Sensitive" first components also include those components that may require special storage and/or handling until just before addition to a second component, for example, refrigeration, desiccation, or heating; as well as first components that for any other reason(s) are desired to be kept separate from a second component between the time of manufacture and until a later time, such as the time of addition to a second component.

This addition of the selected component C1 may be just after affixing delivery package 14 to main package 12 prior to use of the liquid, for example, for enteral nutrition, in the first embodiment, or at a later time. In all embodiments of the invention herein, the first component and the liquid or other second component C2 in the main package 12 are entirely separate from each other from the time of separate filling of the two separate compartments, until the compartment 18 is manually punctured as provided in the particular embodiment.

Referring in greater detail to the preferred embodiments herein (FIGS. 1–2, 8–9, 16–17), the invention is a device 10 for adding a selected first component C1 to a main package 12, which device keeps the first component from the main package 12 until a selected time before use. The device 10 comprises: a delivery package 14 which is mountable on the outside of the main package 12 either before shipment to a consumer (could be done with either embodiment of the invention herein), or at some selected later time (first embodiment). Delivery package 14 has a delivery end 20, a control opening 22, and a compartment 18 containing the first component C1 mounted inside the cavity 24 at the delivery end 20, so that compartment 18 seals the delivery end with a puncturable seal layer 26. Compartment 18 may entirely fill the delivery package 14 or may be in a cavity 24 therein as shown in FIG. 1.

Figure 3:
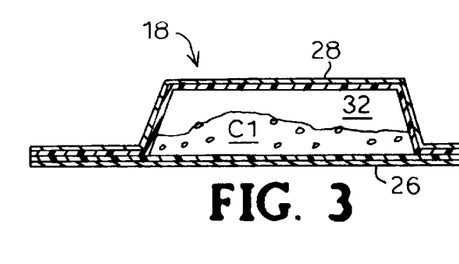
FIG. 3 is a cross-sectional side view of a preferred compartment for use in the invention herein.

As shown in FIG. 3, the compartment 18, which is of a size to hold a predetermined amount of a selected first component, comprises an upper layer 28, a lower layer that is the puncturable seal layer 26, and a compartment cavity 18 between the upper layer 28 and seal layer 26, for holding the first component C1. Compartment 18 is preferably made of foil, and most preferably of foil having a plastic layer on one surface on the outside of the compartment, such as a polyethylene laminated aluminum foil, for example, Catalog No. PETP12 of Danisco (Allborg, Denmark).

Figure 4:
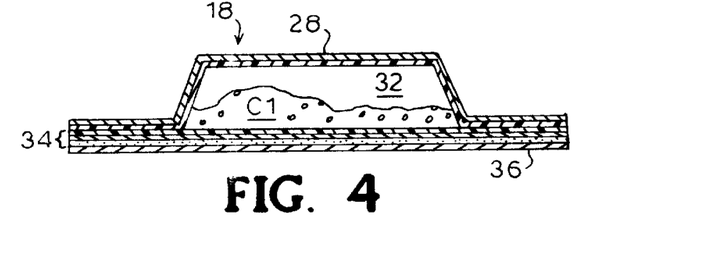
FIG. 4 is a cross-sectional side view of the compartment of FIG. 5 which has an adhesive layer instead of a lower layer, and a removable cover layer attached at its base.

Compartment 18 may be formed by any means known in the art, including means disclosed and discussed in co-pending patent application Ser. No. 08/949,465. Preferably, compartment 18 is a blister pack, as shown in FIGS. 3–4. Blister packs typically have a flat surface sheet (the seal layer 26) sealed to a second sheet (forms the upper layer 28) around the edges of a molded pocket. For use in the invention, the blister-packs are preferably made of plastic-coated foil. Methods of forming blister-packs, including blister-packs where one of the layers is easily releasable from part of the other layer are well-known in the art.

In the first embodiment (FIGS. 1–2), to enable delivery package 14 to adhere to main package 12 at the point where the first component C1 is to be added, an adhesive-coated layer 34 may be provided on the delivery end 20 (FIG. 4), and/or on the compartment 18 itself, which may be in addition to (not shown) or replace the lower layer 26 (as shown in FIG. 4). The adhesive-coated layer 34 has a removable cover layer 36 located over the delivery end 20. This removable cover layer 36 allows delivery package 14 to be affixed to main package 12 preparatory to addition of first component C1 to main package 12.

Inside delivery package 14 is a circular flange 30 which prevents the whole puncturer from being able to fall out backwards from the delivery package 14. Even if the end of the puncturer is pushed up partially it cannot with normal force be pushed entirely out of the delivery package in the wrong direction due to flange 30.

The delivery package 14 also has a puncturer 16 controllable by a user through the control opening 22, for cutting through the compartment 18, the puncturable seal layer 26, and the main package 12 to release the first component C1 into the main package 12 at the selected time. In its preferred embodiments, the puncturer 16, as shown in FIGS. 1–2, comprises an elongated shaft 38 having a pointed puncturing end 40. The elongated shaft 38, has a control portion 46 which may have different configurations, depending on the type of delivery package 14 in which it is mounted. In the preferred embodiment of delivery package, such as for attachment to enteral bags 60 (FIG. 7) or to bottles (FIGS. 8–9), the control portion 46 comprises a plunger portion 48 that extends to the outside of the delivery package 14 (FIG. 1).

Figures 5, 6, 8:
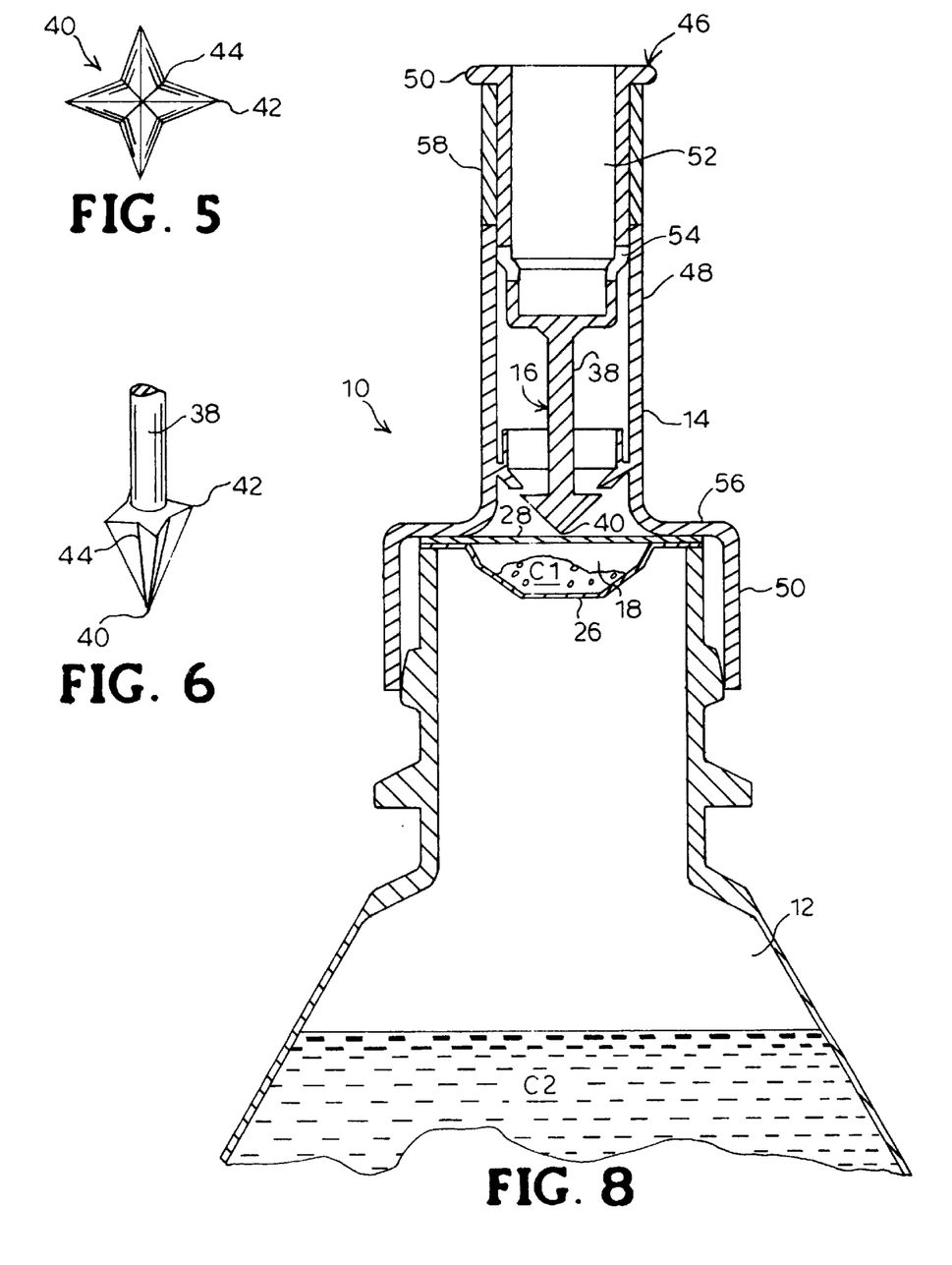
FIG. 5 is a plan view of a first preferred puncturing end of a puncturer having a four-pointed star cross-section.
FIG. 6 is a side perspective view of the puncturing end of FIG. 7.
FIG. 8 is a partial cross-sectional view of the second embodiment of the invention, which is attached to a bottle top, before the puncturer is lowered.
Figure 10:
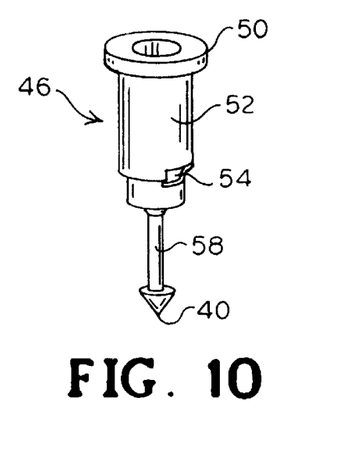
FIG. 10 is a perspective view of a control portion for use in the fourth embodiment of the invention.

The configuration of the pointed end 40 of the puncturer may be tailored for different types of puncturable materials. Preferably, the pointed end 40 is a simple conical shape as shown in FIGS. 1–2. Most preferably, as shown in FIG. 10 discussed below, the pointed end is a simple cone without protrusions. Alternatively, the pointed end 40 may be conical with a serrated or scalloped cross-section, as shown in FIGS. 5–6 with 3–5 equal-sized protrusions extending out from the central axis of end 40, and most preferably 4 protrusions 42 as shown FIG. 5. The indentations formed between the protrusions 42 allow air to move past pointed end 40 as the puncturer 16 moves downward and allow powder and/or granules forming the first component C1 to move past the puncturer 16 into the main package 12 (generally, containing the second component C2) after the compartment 18 and main package 12 are punctured. Liquid from the main package 12 can move through the indentations 44 between the protrusions 42 of the puncturing end 40, into cavity 24, and up the central area of the drinking mechanism of the prior bottle caps so that the beverage to which first component C1 has been added can be consumed.

In each embodiment of the invention herein, depression of the control portion 46 causes the puncturer 16 to move downward toward the compartment 18, ultimately puncturing, in order, the upper layer 28 of the compartment, the lower layer 26 of the compartment 18, the adhesive coated layer 34 (if present), and an outside layer of the main package 12 where the delivery package 14 has been affixed.

Figure 11:
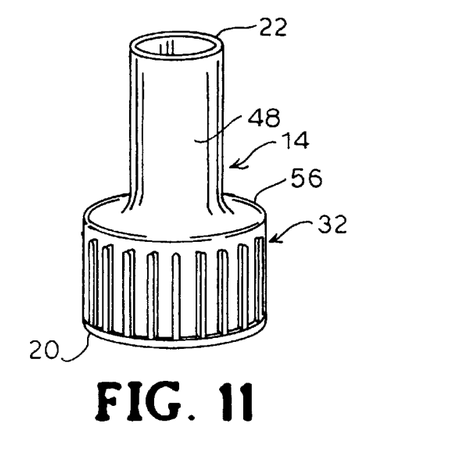
FIG. 11 is a perspective view of a delivery package of the fourth embodiment of the invention.
Figure 12:
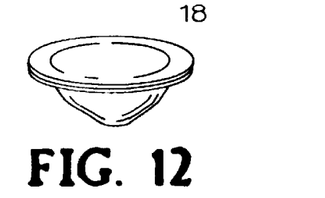
FIG. 12 is a perspective view of a compartment for use in the fourth embodiment of the invention.
Figure 13:
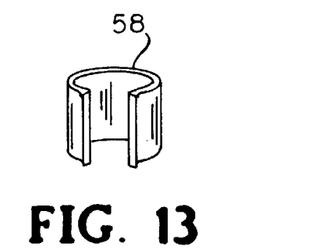
FIG. 13 is a perspective view of a retainer used on the fourth embodiment of the invention.
Figure 14:
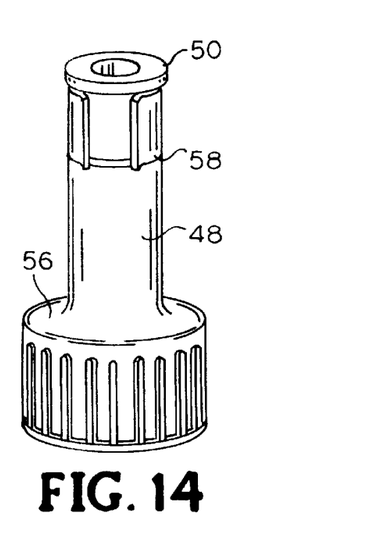
FIG. 14 is a perspective view of the assembled fourth embodiment of the invention before lowering of the control portion to puncture the compartment.
Figure 15:
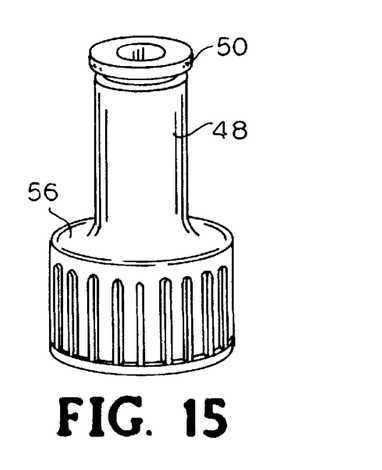
FIG. 15 is a perspective view of the assembled fourth embodiment of the invention after lowering of the control portion.

In the preferred second embodiment of delivery package 14 for attachment to a beverage bottle, the puncturer 16 is positioned within a modified drink-bottle cap 32 (FIGS. 8–9), such as is normally used for sports beverages and the like (see for example U.S. Pat. No. 5,104,008). In this embodiment of the invention, the delivery package 14 is in the form of a screw-on bottle cover as shown in FIG. 11, preferably used with a drink-type bottle. The delivery package 14 has a tubular top extension into which a control portion 46 as shown in FIG. 10 is inserted. The control portion comprises an upper flange 50, a hollowing drinking portion 52 having one or more, preferably two, side openings, and a puncturer, comprising an elongated shaft 38 and a conical pointed puncturing end 40. The compartment 18, containing the first component C1, is mounted inside cavity 24 beneath shoulder 56 of the delivery package 18, shown in FIGS. 8–9, at the delivery end 20, so that compartment 18 seals the delivery end as in the other embodiments. A clip-on retainer 58, shown separately in FIG. 13, snaps on to the top of the of the hollow drinking portion 52 of the control portion 46 beneath flange 50 and keeps control portion 46 from puncturing the delivery package before intended use of the device 10 as shown in FIGS. 8 and 14. When the device 10 is to be used, the retainer 58 is removed, control portion is pushed downward so that the pointed puncturing end 40 goes through the upper layer 28 and lower layer 26 of compartment 18 (FIGS. 9 and 15), releasing the first component C1 into the main package 12. The combined components may then be drunk through the hollow drinking portion 52, as liquid enters it from the main package 12 through the side openings 54.

The main package 12 in the first embodiment may have a port such as is to those known in the art and is formed by a hole in a cardboard layer at one location on the main package 12, forming the top, beneath which is a thin, cuttable foil layer.

Figures 16, 17:
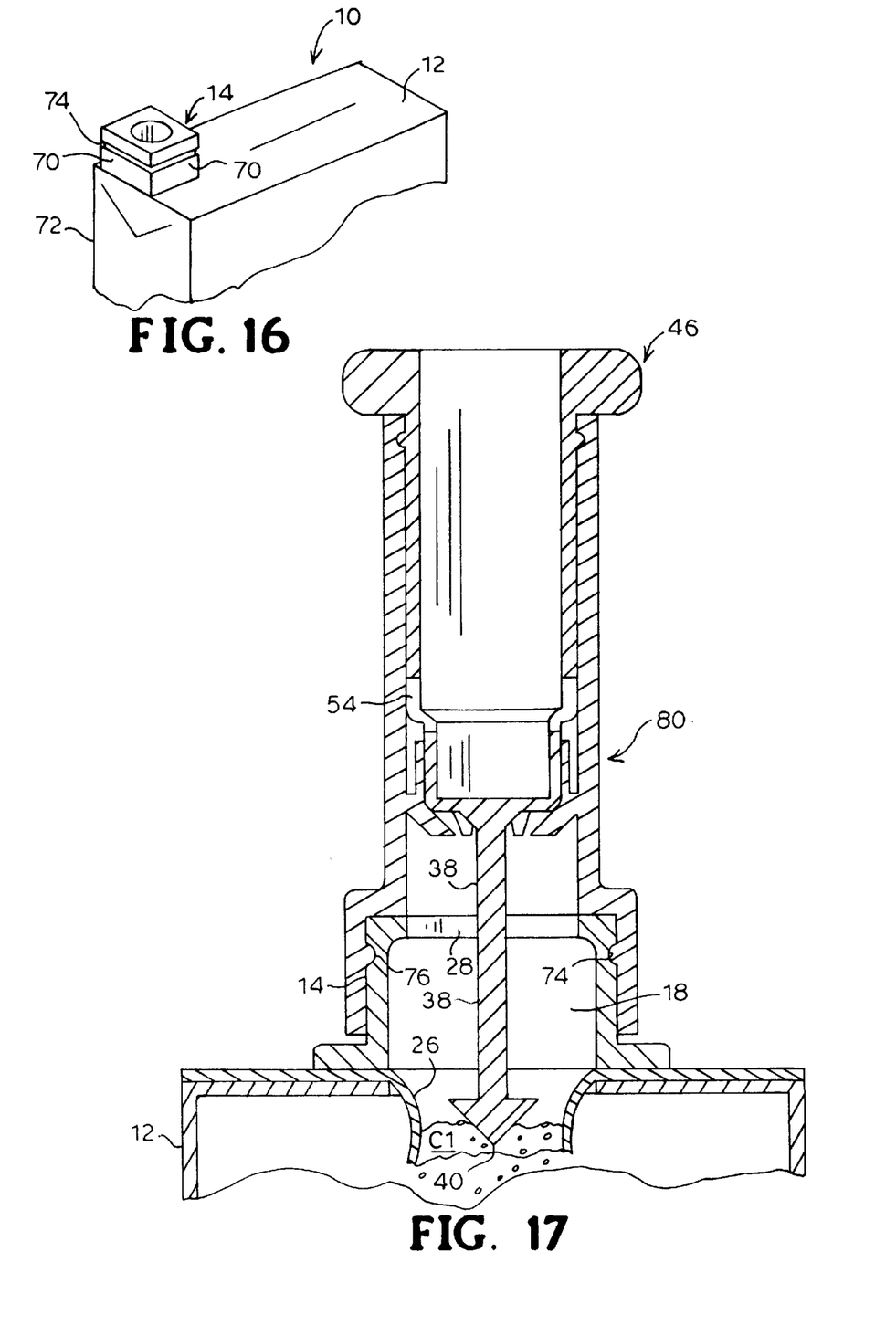
FIG. 16 is a partial perspective view of the top of a main package of the third embodiment of the invention, showing the attached delivery package.
FIG. 17 is a partial cross-sectional side view of the third embodiment of the invention after the puncturer is lowered through the delivery package.

In the third embodiment of the invention shown in FIGS. 16–17, the delivery package 14 is a generally rectangular box placed on top of a main package 12, which may, for example, be a small juice box as is known in the art, as is partially shown in FIG. 16. The delivery package 14 containing first compartment 18 is mounted over a puncturable cover over a hole as is known in the art, and is preferably oriented so that two of the sides 70 of the delivery package align with the corner 72 of the main package as shown. The delivery package 14 has an external means for attachment of a puncturing unit as shown in FIG. 17. Preferably the external means comprises a groove 74 in the four sides of the delivery package 14, and a corresponding inner ridge on a lower rectangular portion 78 of a separate puncturing unit, which unit is size to fit snugly over the delivery package 14. The puncturing unit 80 is attached to the delivery package preferably just prior to use. Lowering the control portion 46 to the position shown in FIG. 17 causes the pointed puncturing end 40 to puncture the top and bottom of the delivery package 14 releasing the first component C1, if present, into the main package. The top and bottom are preferably made of a good moisture and oxygen barrier, such as aluminum or polymers as known in the art. In this third embodiment, the delivery package 14 may actually be provided solely as a means of attaching the puncturing unit 80 to the main package 12, and may not contain any component to be added to the main package 12. Whether or not the delivery package contains a first component C1, the puncturing unit 80 may be structured as discussed above for the second embodiment so that the user can drink from the liquid in the main package through the puncturing unit. Thus, the invention of this embodiment may be used in the same manner as a sports bottle, with the user being able to drink from the main package alternating with closing the package by raising the control portion 46 (as is shown in FIG. 8 in the second embodiment) so that the liquid does not leak out. This allows a standard beverage box to be closed after opening, unlike use of a puncturing straw with such a drink box as is known in the art. During shipment and before use, shrink-wrap or another type of over-cover (not shown) is preferably placed over the exposed part of the control portion 46 from which the consumer will ultimately drink.

When there is a first component, it is preferred that the first component be in the form of a powder that is stable when dry and that is easily dissolved or suspended in the liquid in the main package. A new formulation has been developed for use when dried microorganisms, for example, *Lactobacillus reuteri* cells comprise the active ingredient, or one of the active ingredients, of first component C1. This formulation comprises four main components in the preferred embodiment: (1) the active substance, in this instance, a probiotic comprising lyophilized living bacterial cells; (2) a sugar, preferably a mixture of agglomerated sucrose and standard dextrose; and (3) a salt, preferably NaCl. A formulation of 83% agglomerated sucrose, 10% dextrose, 4% NaCl and 3% *Lactobacillus reuteri* is a typical formulation.

The formulation is then cold-compacted in a cold-compactor, and milled to granules in a suitable mill. Preferably low pressures, in the range of 10–15 KNewton, are used in the compaction so that the bacterial cells are not destroyed. Alternatively, the formulation may be dry blended. In this case, only the agglomerated sucrose (around 97%) and *L. reuteri* (3%) are needed. The cold-compacted granule is preferred as it guarantees a homogeneous material that easily flows into the liquid when the puncturer is used to puncture the main package 12., including compacting the formulation into a sheet of powder.

Effervescent formulations are not preferred because they have been found to interfere with bacterial viability. If allowed in the particular product, for example, in certain pharmaceutical products (but generally not allowed in foods), surfactants such as sodium lauryl sulfate (SLS) or TWEEN 80™ (polyoxyethylene (20) sorbitan monooleate) may also be used. The amount of surfactant is particularly important to ensure that the bacterial cell membranes are not broken down during storage but that there still is sufficient surfactant to cause the bacteria (e.g., $10^8$ bacteria in 300 mg formulation per liter liquid) to disperse evenly in solution in about 5–8 seconds when added to the main package.

Figures 7, 9:
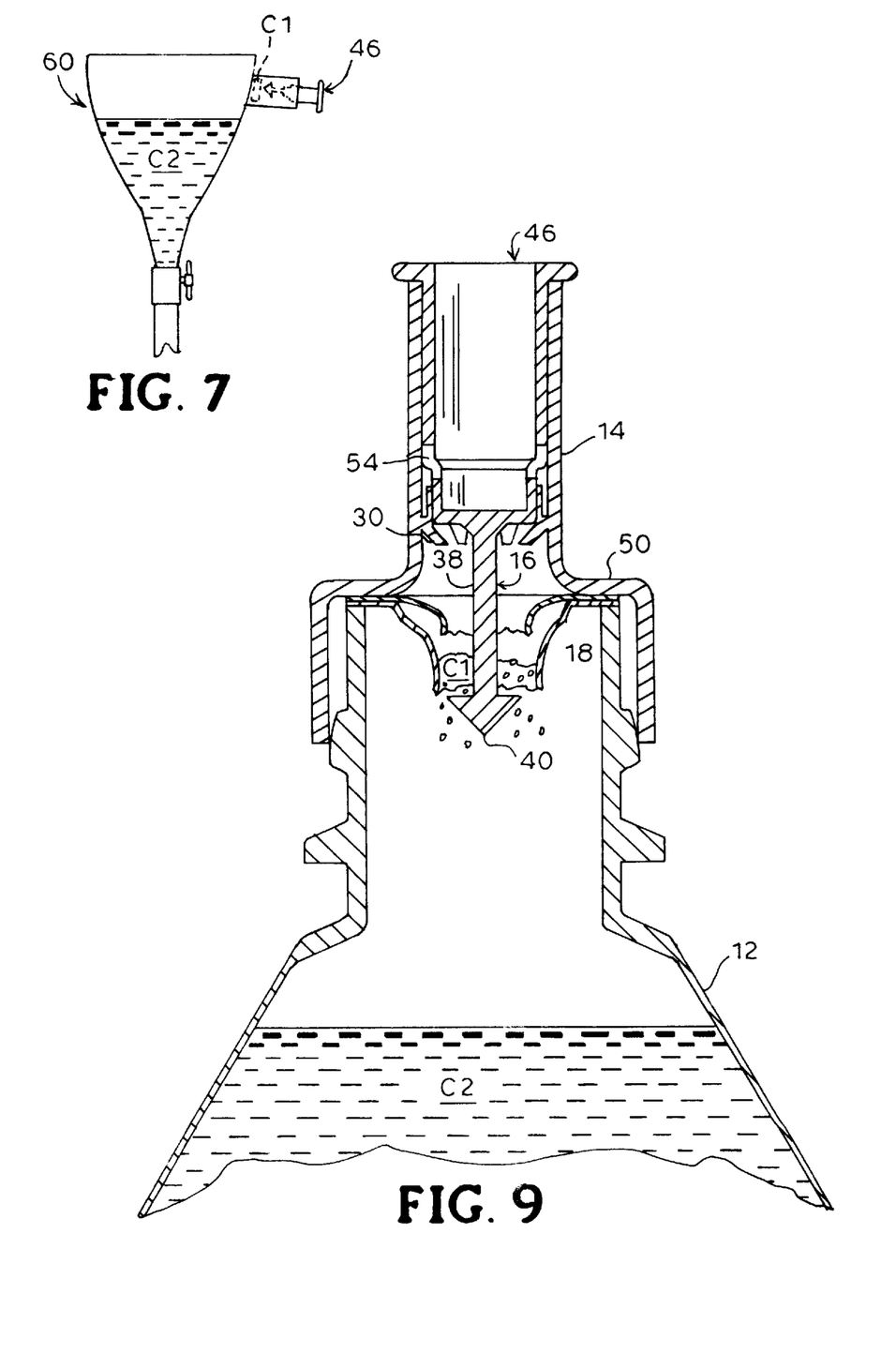
FIG. 7 is a partial schematic diagram of the first embodiment of the invention attached to an enteral bag known in the art.
FIG. 9 is a partial cross-sectional view of the second embodiment of the invention after the puncturer is lowered.

The invention is particularly useful for adding unstable and/or sterile components to a beverage, liquid enteral nutrition or medicine, for example, adding vitamins or beneficial gastrointestinal microorganisms, such as *Lactobacillus reuteri*, to fruit juice, milk, water, medicine, and the like to an enteral bag (FIG. 7). Additional uses include for addition of tablets that form carbonation upon the addition to liquid for creation of carbonated beverages just prior to drinking or for medicinal use.

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. A device that is attachable to the outside of a main package comprising: a delivery package which is mountable on the main package, said delivery package having a delivery end, a control opening, a tubular top extension, and a cavity within the tubular top extension, said cavity extending between the delivery end and the control opening; said delivery package sealed at the delivery end with a puncturable seal; and a puncturer having an elongated shaft within the tubular top extension, said puncturer having a control portion attached to the elongated shaft and inserted into the tubular top extension, said puncturer being controllable by a user through the control opening by movement of the control portion, for cutting through the puncturable seal, and through the main package so that the user has access to the main package at a selected time, wherein said control portion has a hollow drinking portion through which the user may drink from the main portion after the seal and main package are cut by the puncturer.

2. The device of claim 1, further comprising a first component within the cavity.

3. The device of claim 1, wherein the first component comprises a bacteria-containing powder formulation.

4. A device for adding a selected first component to a main package, which device keeps the first component from the main package until a selected time before use, comprising: a delivery package which is mountable on the main package, said delivery package having a delivery end, a control opening, a tubular top extension, and a cavity within the tubular top extension, said cavity extending between the delivery end and the control opening; said delivery package having a compartment at the delivery end that contains a first component, said compartment mounted inside the cavity so that it seals the delivery end with a puncturable seal; and said delivery package having a puncturer having an elongated shaft within the tubular top extension, said puncturer having a control portion attached to the elongated shaft and inserted into the tubular top extension, said puncturer being controllable by a user through the control opening for cutting through the compartment, the puncturable seal, and the main package to release the first component into the main package at the selected time wherein said control portion has a hollow drinking portion through which the user may drink from the main portion after the compartment, seal and main package are cut by the puncturer.

5. The device according to claim 4, wherein the main package contains a second component to which the first component is added.

6. The container according to claim 4, wherein the puncturable seal is made of plastic-coated foil.

7. The device according to claim 4, wherein the main package is an enteral bag and the delivery package is mountable on an outside surface of the main package.

8. The device according to claim 4, wherein the main package is a beverage container having a cap and a movable closure portion, and the delivery package is mounted within the cap and attached to the movable closure portion.

9. The device according to claim 4, wherein the compartment is made of plastic-coated foil.

10. The device according to claim 4, wherein the puncturer comprises a plunger portion which extends through the control opening to allow a user to depress the puncturer.

11. The device according to claim 4, wherein there is a port on the main package for mounting of the delivery package.

12. A method of forming a two-part container, comprising:

(a) providing a device according to claim 4; and (b) attaching the delivery end of the delivery package to an enteral bag.

13. A method of forming a two-part container, comprising providing a device according to claim 5.

14. A device that is attachable to the outside of a main package comprising: a delivery package which is mountable on the main package, said delivery package having a delivery end, a control opening, a tubular top extension, and a cavity within the tubular top extension, said cavity extending between the delivery end and the control opening; said delivery package sealed at the delivery end with a puncturable seal; and a puncturer having an elongated shaft within the tubular top extension, said puncturer having a control portion attached to the elongated shaft and inserted into the tubular top extension, said puncturer being controllable by a user through the control opening by movement of the control portion, for cutting through the puncturable seal, and through the main package so that the user has access to the main package at a selected time.

* * * * *